United States Patent
Maginnis et al.

(10) Patent No.: US 9,874,467 B2
(45) Date of Patent: Jan. 23, 2018

(54) MEMS THERMAL FLOW SENSOR WITH COMPENSATION FOR FLUID COMPOSITION

(71) Applicant: MEMSIC, INC., Andover, MA (US)

(72) Inventors: Thomas O. Maginnis, Dracut, MA (US); Nan Jou Pern, Andover, MA (US); Zhengxin Zhao, Medford, MA (US); Yongyao Cai, Acton, MA (US); Yang Zhao, Andover, MA (US)

(73) Assignee: ACEINNA, INC., Andover, MA (US)

( * ) Notice: Subject to any disclaimer, the term of this patent is extended or adjusted under 35 U.S.C. 154(b) by 196 days.

(21) Appl. No.: 15/047,839

(22) Filed: Feb. 19, 2016

(65) Prior Publication Data

US 2016/0245681 A1   Aug. 25, 2016

Related U.S. Application Data

(60) Provisional application No. 62/119,421, filed on Feb. 23, 2015.

(51) Int. Cl.
*G01F 1/696* (2006.01)
*G01F 1/684* (2006.01)
(Continued)

(52) U.S. Cl.
CPC ............ *G01F 1/6845* (2013.01); *G01F 1/688* (2013.01); *G01F 15/046* (2013.01);
(Continued)

(58) Field of Classification Search
CPC ..... G01F 1/00; G01F 1/12; G01F 1/50; G01F 1/25; G01F 7/00; G01F 25/00;
(Continued)

(56) References Cited

U.S. PATENT DOCUMENTS 4,885,938 A * 12/1989 Higashi ................. G01F 1/684
73/204.18
4,956,793 A * 9/1990 Bonne ..................... G01N 9/04
374/43

(Continued)

FOREIGN PATENT DOCUMENTS

DE    102013105993    *   7/2014    ............. G01N 25/18

OTHER PUBLICATIONS

Translation of DE 101013105993 A1.*
Sagi, et al. In Line Flow-Meter Calibration Advance Methods and Solutions, ATC, Inc. (1997); Revised Dec. 2, 2002.

*Primary Examiner* — Lisa Caputo
*Assistant Examiner* — Nathaniel T Woodward
(74) *Attorney, Agent, or Firm* — Preti Flaherty Beliveau & Pachios LLP

(57) ABSTRACT

The present invention provides a MEMS thermal flow sensor or meter for measuring the flow rate of a fluid without need for calibration of the flow sensor for that particular fluid. A response curve is determined by plotting the sensor output voltage against the volume flow rate divided by fluid thermal diffusivity for a calibration fluid of known thermal diffusivity, and storing response curve data in memory. A conversion factor is employed to provide a measure of correct flow rate of an unknown fluid. This conversion factor is derived from the ratio of the thermal time constant of the calibration fluid to the thermal time constant of the measured fluid, the time constants being measured at zero flow. These time constants are stored in memory. This conversion factor in conjunction with the response curve data is utilized by the processor to produce the correct flow rate. The invention also encompasses a method for measuring fluid flow rate of fluids of differing properties without necessity of a separate flow calibration for each fluid.

9 Claims, 8 Drawing Sheets

(51) Int. Cl.
  *G01F 25/00* (2006.01)
  *G01F 1/688* (2006.01)
  *G01F 15/04* (2006.01)
  *G01F 1/36* (2006.01)
  *G01N 11/08* (2006.01)

(52) U.S. Cl.
  CPC ............ *G01F 25/0053* (2013.01); *G01F 1/36* (2013.01); *G01N 11/08* (2013.01)

(58) Field of Classification Search
  CPC ...... G01C 25/00; G01D 18/00; G01D 18/008; G01D 3/02; G01D 3/022; G01K 15/00; G01R 35/00; G01R 35/005; G06F 17/00
  See application file for complete search history.

(56) References Cited

U.S. PATENT DOCUMENTS

| | | | | |
|---|---|---|---|---|
| 5,285,673 A | * | 2/1994 | Drexel | G01F 1/6888 73/1.16 |
| 5,359,878 A | * | 11/1994 | Mudd | G01F 1/6847 73/1.16 |
| 5,944,048 A | * | 8/1999 | Bump | G01F 1/6842 137/486 |
| 6,272,919 B1 | * | 8/2001 | Huiberts | G01F 1/6842 73/204.18 |
| 6,449,571 B1 | * | 9/2002 | Tarig | G01F 1/6965 137/486 |
| 8,746,032 B1 | * | 6/2014 | Feller | G01F 25/0007 73/1.35 |
| 9,605,992 B2 | * | 3/2017 | Smirnov | G01F 25/0007 |
| 2006/0272385 A1 | | 12/2006 | Lewis | |
| 2008/0000283 A1 | * | 1/2008 | Wang | G01F 1/6842 73/1.16 |
| 2008/0210306 A1 | | 9/2008 | Xie et al. | |
| 2011/0247390 A1 | * | 10/2011 | Smirnov | G01F 25/0053 73/1.16 |
| 2013/0060492 A1 | | 3/2013 | Stabile, Jr. et al. | |
| 2013/0124112 A1 | | 5/2013 | Heath et al. | |
| 2014/0092935 A1 | | 4/2014 | Lin et al. | |
| 2014/0345363 A1 | * | 11/2014 | Pretre | G01N 25/18 73/25.03 |

\* cited by examiner

MEMS THERMAL FLOW SENSOR WITH COMPENSATION FOR FLUID COMPOSITION

BACKGROUND OF THE INVENTION

This invention relates to a thermal mass flow meter of the MEMS variety, in which the flow sensor is constructed by micromachining techniques on a silicon substrate, and employs a central heater flanked by two or more upstream and downstream temperature detectors all placed in direct thermal contact with the flowing fluid, so that the existence of fluid flow in the upstream or downstream direction causes an imbalance in the temperature detectors indicative of the fluid flow rate. The flow sensor is fabricated on the surface of a silicon crystal and then mounted either as part of an inside wall of a flow channel that carries the fluid flow, or on a membrane or bridge structure that spans the flow channel internally.

Such MEMS flow sensors are known to have output that is sensitive to the thermal and mechanical properties of the fluid flowing through the sensor, such as fluid mass density, specific heat, thermal conductivity, viscosity, etc. and also to environmental variables such as fluid inlet temperature and pressure. These dependencies limit the ability of a user to operate the flow sensor with different fluids and fluid mixtures, unless expensive and time consuming empirical calibration of the MEMS flow sensor with each fluid of interest is first performed.

It is therefore desirable and useful to provide a method of automatically correcting the output of a MEMS thermal flow sensor for different fluid compositions by direct measurement of the relevant fluid properties performed within the flow sensor itself. The invention disclosed below teaches a method for accomplishing this fluid composition correction, enabling a thermal flow sensor calibrated once on a known fluid to measure a wide variety of unknown pure fluids and fluid mixtures without further flow calibration, provided only that a time constant and thermal conductivity representative of the unknown fluid or mixture are first measured within the flow sensor at zero flow.

Note that "fluid" as used in this document denotes any material medium that is capable of flowing through a conduit and being heated or cooled, for example gases, liquids, granular materials, suspensions, mixtures, etc. The principles of thermal flow sensing apply to all fluids in this wider sense. Also, use of the more specific terms gas, liquid, mixture, etc. to describe specific implementations below should not be interpreted in a limiting sense but as instances of "fluids" in the broader sense.

Two other kinds of commercially relevant thermal flow meters exist in the prior art. First are the large insertion probe thermal flow meters that typically use a macroscopic inserted probe that measures flow at one point on the cross-sectional area of the pipe, and typically operate in the turbulent flow regime. In these designs the thermal detectors are not in direct contact with the flowing fluid, but reside behind the protective walls of the metal (typically stainless steel) probe that projects inward radially from the pipe wall where it is attached. These meters must be flow calibrated with the user fluid. They are a direct commercial evolutionary development of the hot-wire anemometers, primarily used for fluid flow research, that are too fragile for use in industrial applications. These insertion probe thermal meters are not used for the same applications, or in the laminar flow regime served by the MEMS variety of thermal flow sensors. They will not be further discussed here. However their characteristics and guidelines for their use are summarized in the two international flow standards, one from ISO, and one from ASME, listed in the References section.

Another kind of thermal flow meter known in the art is the capillary tube thermal flow meter, which has external heating and temperature resistive sensing coils wound on the outside of a small capillary tube, the sensing coils not in direct thermal contact with the flowing fluid, but measuring the temperature of the tube wall that is in direct thermal contact with the flowing fluid at the tube wall inside surface. These flow meters also have sensitivity to fluid or gas composition, but their gas composition dependence is much better understood than the gas composition dependence of MEMs thermal flow meters.

The capillary tube thermal mass flow sensors exhibit at low laminar flows a response that is directly proportional to mass flow rate for all fluids, with a slope that is fluid-dependent. At high laminar flow rates, however, their response becomes a non-linear function of mass flow, that has a more complicated dependence on fluid composition and properties. As first suggested by Blackett (P. M. S. Blackett Proc. Roy Soc. 1930, p. 319 ff), in their linear response range to flow, the capillary tube thermal flow meters respond in direct proportion to the heat capacity per unit time flowing through the tube, and are otherwise independent of fluid composition. Therefore, if the fluid heat capacity per unit mass is known, the capillary meter may be calibrated to read mass flow directly without the requirement to know any other fluid properties. For this technology it is also a simple matter to convert a flow rate measured with one fluid to a flow rate measured with a second fluid passing through the same calibrated flow sensor, by multiplying the sensor flow rate reading by a gas or fluid correction factor. The gas correction factor is simply the ratio of the heat capacities of the two known fluids in the flow region where the sensor response is linear with both fluids. Therefore a capillary thermal flow sensor calibrated on fluid A may be used to measure flow of any known fluid B if the readings are multiplied by the constant gas correction factor that connects fluids A and B. Such capillary tube thermal flow meters are unable to measure the flows of arbitrary unknown pure gases or mixtures, where the gas or gas mixture specific heat capacity is variable or unknown, though they will still respond in proportion to the mass flow rate, i.e. for unknown gases of constant composition they behave like a flow meter that is not calibrated. As they have no way to distinguish a changing fluid specific heat from a changing fluid mass flow rate, being sensitive only to the product of the two quantities, the capillary tube thermal sensors cannot be used directly to measure the flow rate of a fluid mixture that has time-varying composition.

As Blackett also pointed out, at sufficiently high flows the capillary tube flow sensor response becomes a non-linear function of flow rate, responding now also to the cube of the flow rate and not just to the first power of flow. However, the cubic term depends in addition on the fluid thermal conductivity, and so at higher flows the simple gas conversion by gas heat capacity no longer holds, and the gas conversion becomes much more complicated. For this reason capillary tube mass flow meters and mass flow controllers are normally operated only in the linear response range of the capillary tube thermal flow sensor, where a constant gas correction factor independent of flow is sufficient for the conversion between flows of different known gases or mixtures of gases of known fixed proportions. The ISO standard for thermal flow meters cited above also describes features and use of capillary tube thermal flow meters and controllers operated in the linear portion of their flow response, including the routine use of gas correction factors for employing a meter calibrated on one gas to measure mass flow rates of other gases of known specific heat capacity, without requirement for recalibrating the instrument separately for each different gas or mixture of gases. The Sierra Instruments Inc. White Paper "Capillary Thermal Users Guide" provides a thorough summary of capillary tube thermal sensor flowmeters and controllers operated in the linear response of the flow sensor tube.

There is also a prior art patent for capillary tube thermal flow sensors teaching a method to allow operation with different gases even in the non-linear portion of the sensor flow response range, (Wang, Valentine, & Lull, U.S. Pat. No. 7,043,374, May 9, 2006). This patent may be summarized as follows.

It is asserted that for capillary tube sensors there exists a unique functional relationship between sensor output voltage, S, volume flow rate Q, sensor length L, conduit cross-sectional area A, fluid mass density $\rho$, fluid specific heat at constant pressure $C_p$ and two empirically determined constants that are typically different for each fluid, f and g, such that $$f \cdot \frac{S}{k} = W\left(g \cdot \frac{\rho \cdot Q \cdot L}{A} \cdot \frac{c_p}{k}\right) \quad (1)$$

Here W stands for a unique capillary sensor response function that is the same for all fluids and all sensors of a specific design. The assertion is that if the quantity on the left of equation (1) is considered to be a y coordinate, and the quantity in parenthesis on the right of Eq. (1) is considered to be an x coordinate, then a plot of y(x) based on measured sensor output S as a function of measured volume flow rate Q will give a unique nonlinear curve y(x) that is independent of gas or gas mixture species, despite the fact that S(Q) plotted vs. Q gives different curves for different gas and mixture species. To determine the flow of a gas of known composition from the relation of Equation (1), starting from the measured sensor voltage S, one must calculate the corresponding y from measured S and the two known gas properties f, k, then find from y the corresponding x coordinate on the previously determined unique curve y(x), and then use the known gas and dimensional sensor properties g, $\rho$, k, $C_p$, L and A to find the appropriate volume flow Q from the numerical value of the x coordinate of the curve. U.S. Pat. No. 7,043,374 discloses no specific analytical functional form or continuous curve for the function W; it apparently consists only of a set of associated discrete (x,y) points computed from the (S, Q) sensor output points resulting from calibration of the flow sensor on specific known gases. U.S. Pat. No. 7,043,374 also teaches no method for the determination of the empirical gas properties f,g required for each gas to apply the method. This omission is especially glaring in the case of process gases that are so reactive they cannot be safely used in production calibration, so that they are replaced by safer surrogate gases for manufacturing flow calibrations.

In summary, for prior art capillary tube thermal flow sensors operated in the linear portion of the sensor response there is a simple gas properties conversion that allows use of a sensor calibrated on one known gas to be used with many other known pure gases and gas mixtures of constant proportions provided the relative specific heat capacities of the gases or mixtures are all known. This property of capillary tube thermal flow sensors is well-known, and is described for instance in the ISO Standard issued Oct. 15, 2001 and titled "ISO-14511 Thermal Mass Flow Meters in Closed Conduits".

For capillary tube sensors operated in the non-linear portion of the sensor response range the gas dependence is more complicated, and involves other gas properties besides fluid specific heat capacity. The prior art described in US patent by Wang, et al. U.S. Pat. No. 7,043,374 B2 teaches a method of operating such a capillary sensor in the non-linear part of the response curve providing one knows the density, thermal conductivity, and specific heat at constant pressure of each gas, plus the two empirically determined gas constants f and g for each gas, plus the length and cross-sectional area of the capillary tube sensor employed, and that one has previously measured the "characteristic curve" W using the sensor in question for all gases of interest with known properties. Because of the need to measure the new gas properties f and g for each gas of interest, this method is only practical for those with the resources needed to complete the necessary up-front flow testing, or who have access to a manufacturer's database containing this information.

In contrast, MEMS thermal flow sensors have a different dependence on gas properties than the capillary tube flow sensors, even in the linear response range where they have a dependence on fluid thermal conductivity and mass density as well as heat capacity. For example, those familiar with the capillary tube thermal flow meters know that in the linear flow response range of the sensor both hydrogen and air have nearly the same slope vs. standardized volume flow rate, so that the "gas correction factor" is close to 1 for these gases. However, for a MEMS thermal flow sensor with heating and sensing internal to the flow conduit the gases hydrogen and air have dramatically different slopes even in the linear region of the sensor response. Thus the same dimensionless correlation does not apply to both types of thermal flow sensor, and the correlation (1) taught in the prior art of U.S. Pat. No. 7,043,374 is not valid for MEMS thermal flow sensors with heater and temperature sensors directly exposed to the flowing fluid.

Therefore it has not previously been possible to use a MEMS thermal flow sensor with heater and temperature sensors immersed in the flowing fluid to measure flows with many gases based on a single flow calibration with only one gas, even in the linear response range, because no accurate and simple method of gas conversion was known. In addition, it has been the common practice with MEMS flow sensors to calibrate and use them over wide flow ranges where the response is highly non-linear for all gases or fluids used. Therefore it has heretofore been necessary to perform an expensive non-linear calibration with each gas or fluid that one wishes to use in a MEMS thermal flow meter, with the result that the high cost of multiple non-linear calibrations has largely restricted use of the MEMs-based flow meters to flows of the most common gas mixture, air.

SUMMARY

The present invention provides a MEMS thermal flow sensor or meter for measuring the flow rate of a fluid without need for calibration of the flow sensor for that particular fluid. A response curve is determined by plotting the sensor output voltage against the volume flow rate divided by fluid thermal diffusivity for a calibration fluid of known thermal diffusivity, and storing response curve data in memory. A conversion factor is employed to provide a measure of correct flow rate of an unknown fluid. This conversion factor is derived from the ratio of the thermal time constant of the calibration fluid to the thermal time constant of the measured fluid, the time constants being measured at zero flow. These time constants are stored in memory. This conversion factor in conjunction with the response curve data is utilized by the processor to produce the correct flow rate.

The invention also encompasses a method for measuring fluid flow rate of fluids of differing properties without necessity of a separate flow calibration for each fluid.

The flow sensor provides a measure of the volumetric flow rate. A measure of mass flow rate can be provided in accordance with the invention by use of a fluid mass density measuring instrument. For cases where the fluid can be considered a perfect gas, in situ measurements of gas temperature and pressure in combination with volume flow rate can be employed to produce a flow signal directly proportional to the mass flow rate.

Applicant has discovered that for MEMS thermal flow sensors which are operated in a constant temperature rise mode, there is a dimensionless relationship between flow sensor output ($\Delta T/T_{rise}$) and a dimensionless flow variable that is proportional to volume flow rate Q divided by a characteristic length $\sqrt{A}$, further divided by fluid thermal diffusivity $\alpha$. Here $\Delta T$ is the downstream minus upstream flow-induced temperature difference, $T_{rise}$ is the temperature elevation of the MEMS gas heater above thermal ground, and A is the cross-sectional area of the flow conduit at the location of the internal sensor heater element. Of course A is constant for a given sensor design, and does not depend either on flow rate Q or gas thermal diffusivity $\alpha$, so is not material except when comparing responses of sensor designs with different A, and can be dropped to simplify the analysis when only flow responses of different gases in the same sensor are under consideration.

When the sensor output voltage for different fluids and mixtures is plotted against the volume flow rate divided by fluid thermal diffusivity, $Q/\alpha$, a universal response curve that is substantially the same for all fluids results. Therefore once the shape of this curve is determined for one fluid of known thermal diffusivity for a specific MEMS sensor design by a flow calibration, it is possible to predict the sensor flow response curve plotted as a function of volume flow rate for any fluid or mixture of known thermal diffusivity.

To use the method described above also for fluids of arbitrary and unknown thermal diffusivity, it is sufficient to measure a quantity representative of the fluid thermal diffusivity in situ within the flow sensor. Because only the ratio of thermal diffusivities is needed to convert from one gas flow to another, it is not necessary to measure the absolute thermal diffusivity of any gas, but only the relative thermal diffusivities of two gases or mixtures of gases. One can measure a quantity representative of the fluid thermal diffusivity by determining the exponential time constant for the fluid within the sensor volume to reach thermal equilibrium when subjected to a step change in heater power at zero flow. In fact the fluid thermal time constant is inversely proportional to the fluid thermal diffusivity, for usual thermal flow sensor designs. In addition, thermal conductivity can be measured at zero flow comparing the equilibrium temperature. Thermal conductivity is proportional to temperature. This is shown for example, by CFD simulations of temperature response of different gases to a step change in gas heater power, and also by a simple analytical model of the coupled solid and fluid portions within the sensor body.

Therefore, by a zero flow measurement of the thermal time constant of an unknown fluid, compared to the corresponding zero flow thermal time constant of the particular calibration fluid used to perform the flow calibration of the MEMS thermal flow sensor, one has a measure of the ratio of thermal diffusivities of the unknown and known fluids, sufficient to determine from the universal sensor response plot, the correct location on a volume flow rate axis for the unknown fluid, given the sensor voltage output for that fluid at an unknown but constant flow rate. Therefore the method allows the determination of the correct volume flow rate of the unknown (or arbitrary) fluid from the sensor output measured with that fluid flowing at an unknown flow rate, provided one has first determined the time constant for the unknown fluid at 0 flow, and has previously measured the universal sensor response curve for at least one fluid (by actual flow calibration with that fluid).

DETAILED DESCRIPTION OF THE DRAWINGS

Figure 1:
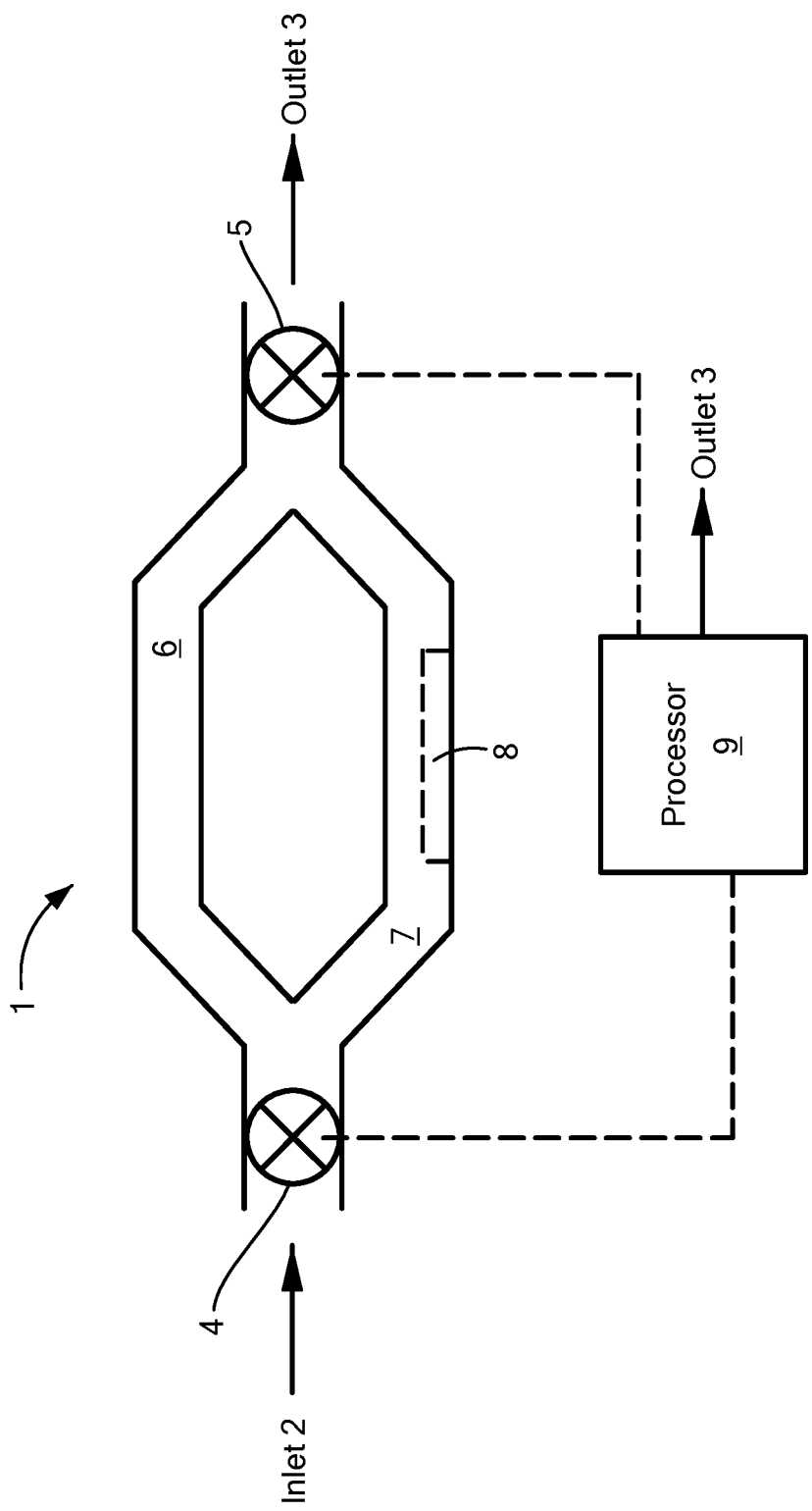
FIG. 1 shows a schematic overview of the entire flow meter, not to scale, showing flow meter body 1, electronics and computer module or processor 9, flow divider and bulk and sensor or bypass flow channels, and signal paths communicating between the thermal sensor and the computing module (dotted lines)

FIG. 1 shows a schematic overview of the entire flow meter, not to scale, showing flow meter body 1, flow inlet 2 and flow outlet 3, inlet positive shut off valve 4 and outlet positive shut off valve 5, flow splitter bulk channel 6 (typically carrying the larger portion of the divided total flow), and sensor or bypass flow channel 7 (typically carrying the smaller portion of the divided total flow), with the thermal flow sensor itself 8 mounted within flow sensor channel 7. A flow sensing chamber is defined in flow channel 7 between valves 4 and 5. After fluid enters and fills the chamber, the shut-off valves are turned off to seal the interior volume inside the chamber where the fluid thermal time constant is measured. The positive shut-off valves may be connected externally and supplied by the meter user, or they may be built into the meter by the manufacturer. Either way they must be in the shut position during the period when the fluid thermal time constant is being measured. Once the fluid thermal time constant has been measured and stored in memory, and the flow meter has been zeroed, the inlet and outlet shut-off valves are opened to allow the meter to pass flow.

The dotted lines in FIG. 1 indicate data communication connections and control signal paths between the flow meter sensing and actuating components (thermal flow sensor and inlet and outlet shut-off valves) and the Electronics and Computing module or processor 9 where the meter operating program and calibration data are stored in memory. The solid arrow pointing away from the processor 9, indicates the information pathway that communicates the meter flow reading to the meter user.

The processor 9 is typically a microprocessor having software or firmware operative to provide the intended computations in accordance with the disclosure herein. The microprocessor per se can be of any known configuration and can be mounted in or in association with the flow sensor body.

Figure 2:
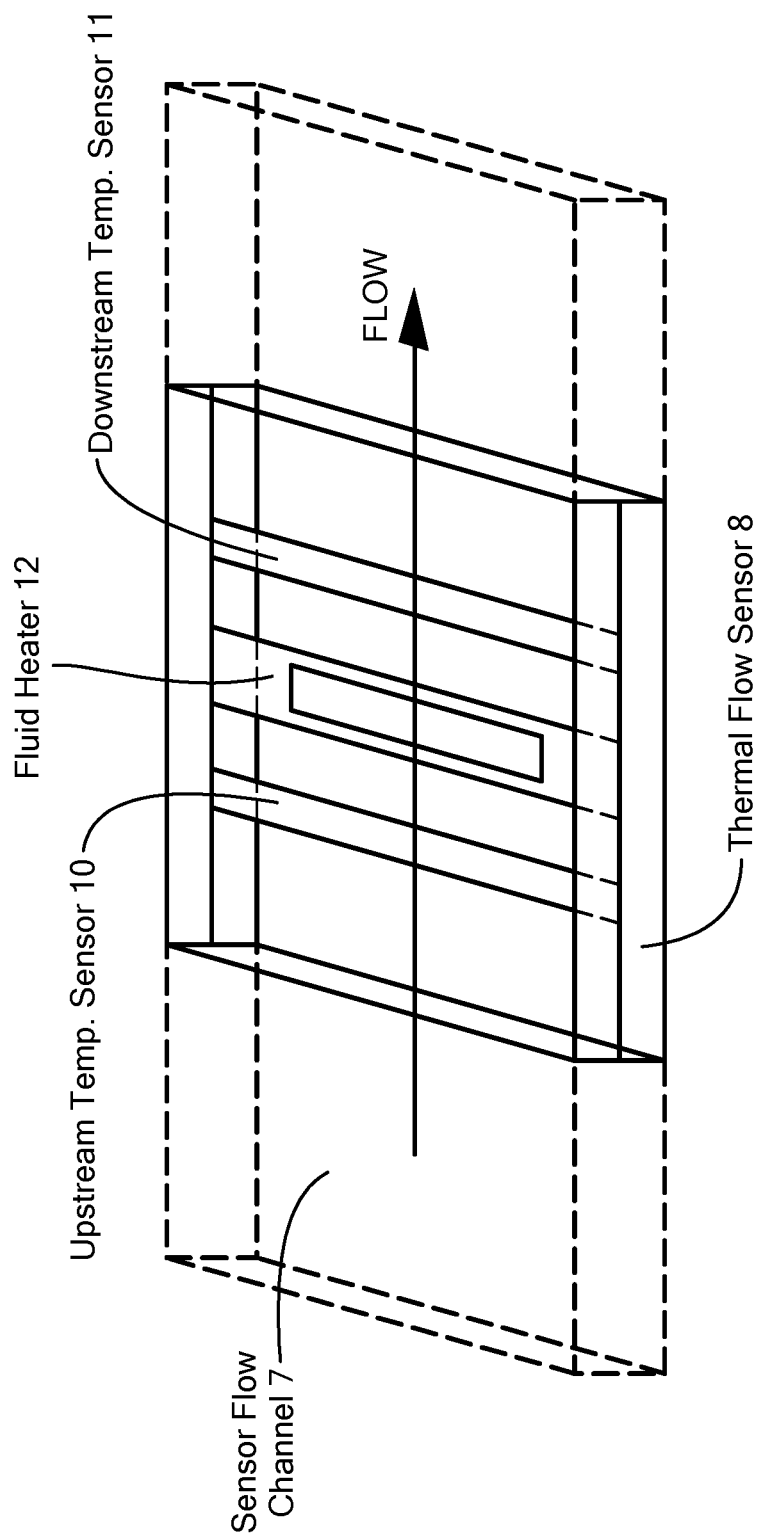
FIG. 2 shows an enlarged schematic view of a portion of the sensor flow channel 6, not to scale, showing the relative spatial positions of fluid heater and up and down stream temperature detectors that measure upstream and downstream fluid temperatures, and their approximate relative locations in the sensor flow channel.

FIG. 2 shows a portion of the sensor flow channel 7 (indicated by dotted lines), where the active components of the thermal sensor 8 are located, that perform the basic measurements that contribute to the meter output flow signal after processing by the processor. These components are micro-bridge fluid heater 12, suspended across the flow channel, and in direct thermal contact with the flowing fluid, upstream fluid temperature sensor 10, and downstream fluid temperature sensor 11, both also suspended by microbridges across the flowing stream of fluid and in direct thermal contact with it.

The expression "direct thermal contact" is intended to include a thermally thin protective surface coating on the heater and temperature sensors that are otherwise immersed in the fluid. To be "thermally thin," the coating must have negligible heat capacity relative to the heat capacity of the heater or temperature sensor itself.

Though a rectangular cross-section sensor flow channel is shown in FIG. 2 for example, the flow sensor channel cross-section shape may be circular, oval, elliptical, triangular, hexagonal or of any constant area closed geometrical form that will generate a generalized cylinder (as distinct from a circular cylinder) when projected along the direction of flow. Similarly, though the fluid heater 12 and upstream and downstream temperature sensors 10 and 11 are depicted as micro-bridges extended across the sensor flow channel they may be of any geometrical form capable of adequately heating the flowing fluid, and of detecting the flow-induced downstream—upstream temperature difference of the fluid.

Figure 3:
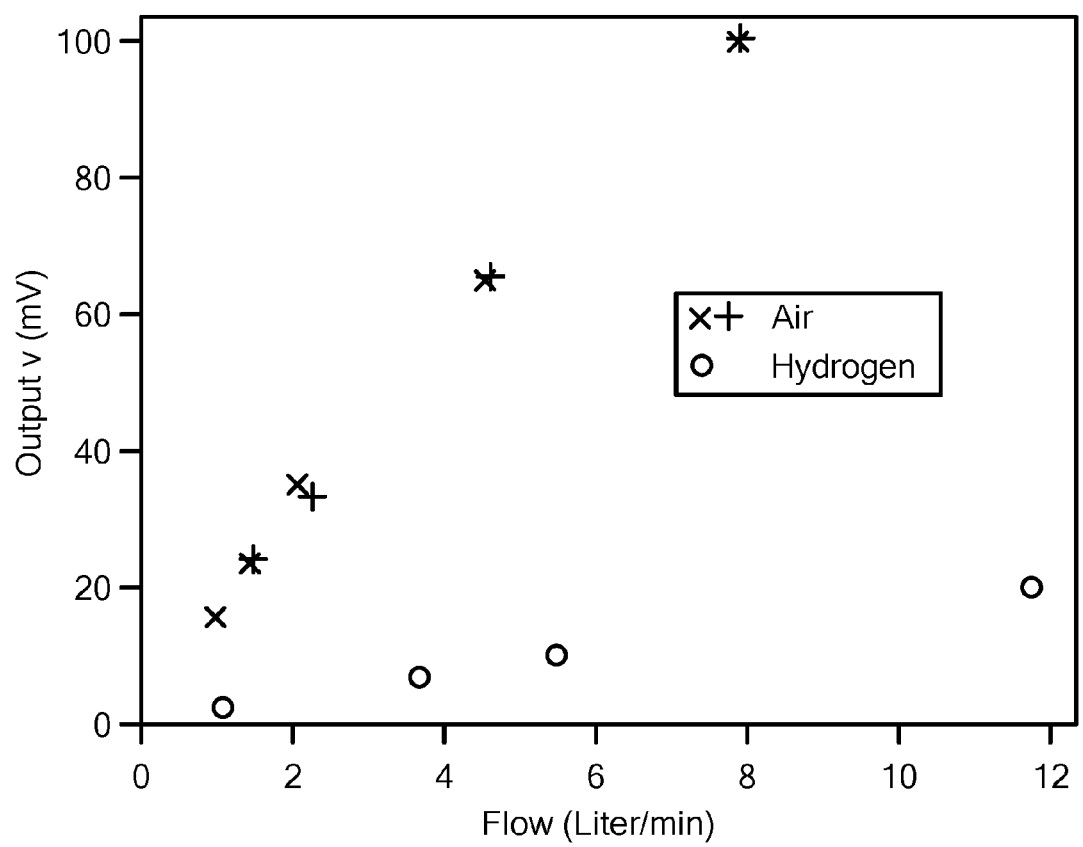
FIG. 3 shows a combined plot of the measured flow responses vs. volume flow rate of a MEMS flow sensor flowing air and then $H_2$ in the linear range of the sensor response, showing widely different slopes, unlike capillary tube responses for the same two gases, that have nearly the same slope.

FIG. 3 is a plot of the measured flow response of a MEMS flow sensor with air and $H_2$ in the approximately linear range of the sensor response. Flows of the two different gases were separately measured in the meter, then the two meter flow responses with the different gases were plotted on the same graph for comparison. The points marked by + and x are two flow runs conducted with air flowing through the flow meter. The points depicted by circles are measurements made in the same meter with hydrogen flowing through the meter. It is immediately apparent that the slope of output voltage vs. volume flow rate for air is not almost equal to the slope with hydrogen, but much larger. The + and x symbols on this plot denote two separate runs with air, and their vertical separation at each flow rate gives an indication of the measurement error. FIG. 3 shows that the MEMS flow sensor has a dramatically different response with the gases air and hydrogen than the well-known capillary tube correlation based on specific heat of the flowing gas or mixture, which predicts a nearly identical response for air and $H_2$ in the linear portion of the flow response. Sierra Instruments Inc., a known manufacturer of capillary type thermal flow meters, gives the conventional gas correction factor (K-factor relative to air) for $H_2$ in their capillary tube thermal mass flow instruments as 1.001. Therefore the MEMS flow sensors respond differently than the capillary tube sensors when different gases are flowed in them, and obey their own independent gas response law. The capillary tube gas conversion factors are in general not valid for MEMS thermal flow sensors.

Figure 4:
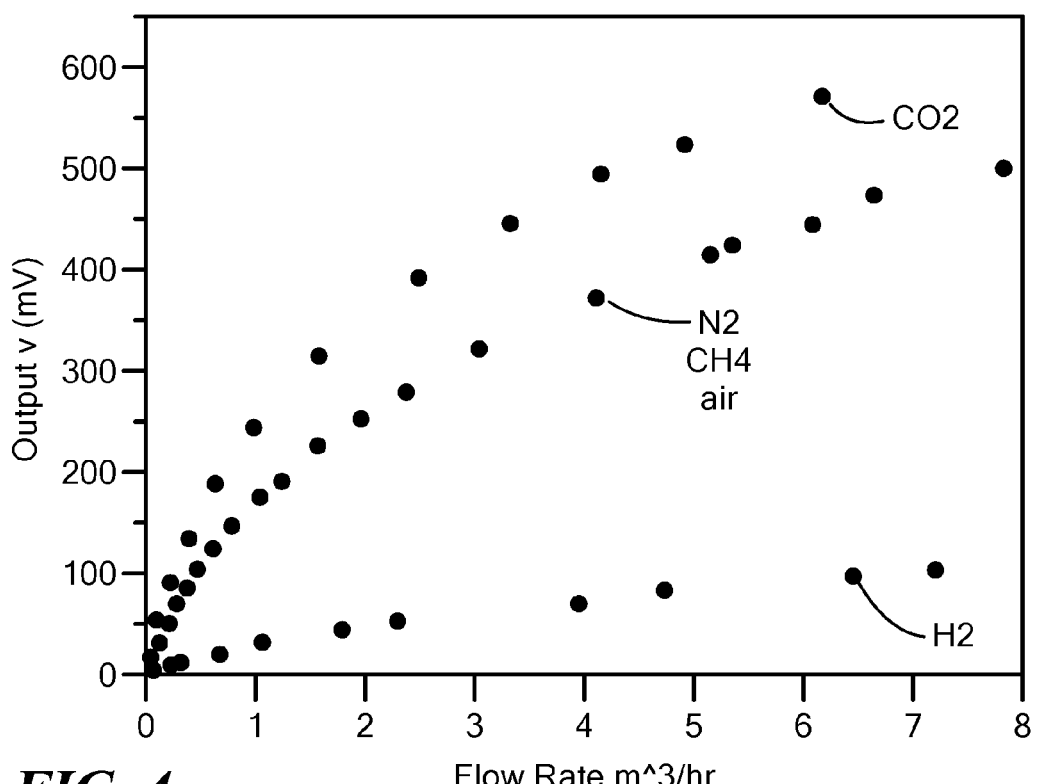
FIG. 4 is plot of the measured flow response vs. volume flow rate of a flow meter for 5 different gases, in the non-linear range of the flow response.

FIG. 4 shows a plot of the raw sensor output vs. volume flow rate of a MEMS flow meter for 5 different gases, in the non-linear range of response. Though some gases ($N_2$, air, $CH_4$) have close responses, nearly independent of gas composition, others, like $CO_2$ and $H_2$, have drastically different responses. There is a particularly large difference between the gases $CO_2$ and Hydrogen. This Figure also exhibits the difference in response between capillary tube flow sensors and MEMS flow sensors for the gases air and methane (CH4), which are nearly identical for the MEMs flow sensor as shown in FIG. 4, but differ by approximately 25% in slope for the capillary tube sensors (Sierra Instruments (op. cit.) gives methane gas correction factor relative to air as 0.754). a FIG. 4 is provided to illustrate a before and after comparison to the similar plot of FIG. 5, where the flow axis is rescaled by dividing measured volume flow rate by the thermal diffusivity of each gas measured.

Figure 5:
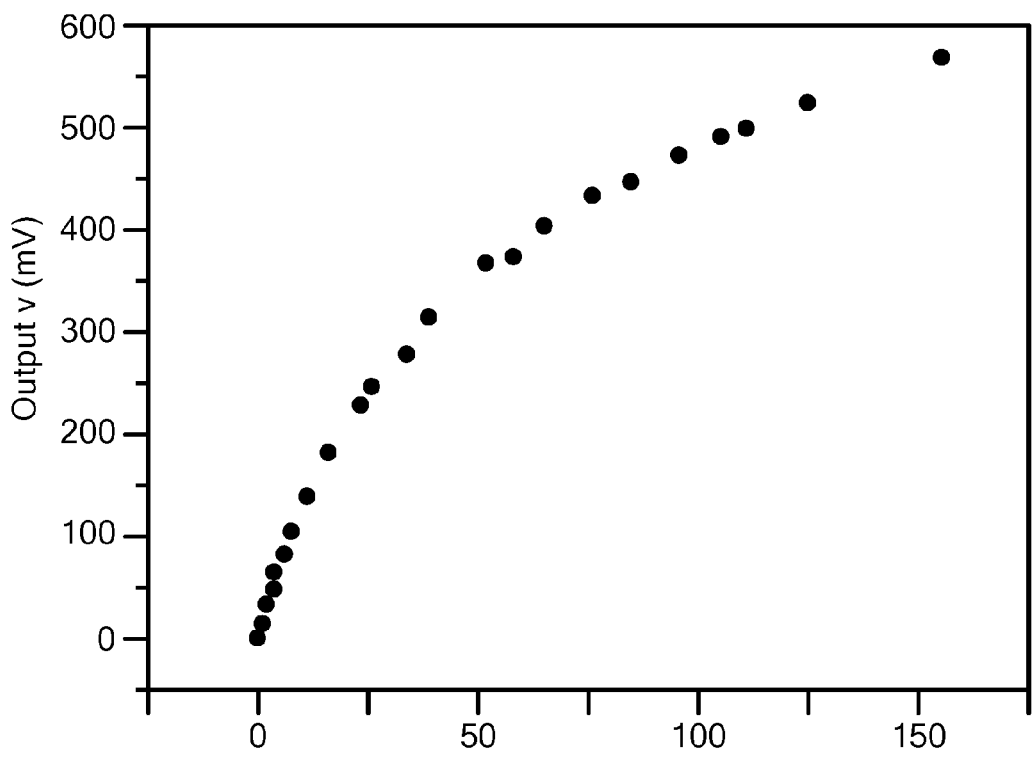
FIG. 5 Plot of the measured flow response vs. rescaled flow rate [(volume flow rate)/(fluid thermal diffusivity), $Q/\alpha$] of a flow meter for 5 different gases in the non-linear part of its range.

FIG. 5 shows a plot of the raw flow meter output vs. Q/α for the same flow data earlier plotted in FIG. 4 (before flow rescaling). Here Q is the measured volume flow rate for each gas, as in FIG. 4, and α is the thermal diffusivity of that gas. This horizontal axis is the rescaled flow axis according to the correlation of the present invention. It is evident that the five different response curves have been substantially collapsed into a very tight cluster of nearly coincident curves. This is in sharp contrast with FIG. 4, where the correlation is not employed. Though the flow meter employed in the tests of FIGS. 4 and 5 is not optimal for the use of the rescaled flow plot, because of its design, it still shows a substantial progress in getting the disparate curves of FIG. 4 to converge toward a universal curve. Other improved designs should produce even better convergence with different gases.

Figure 6:
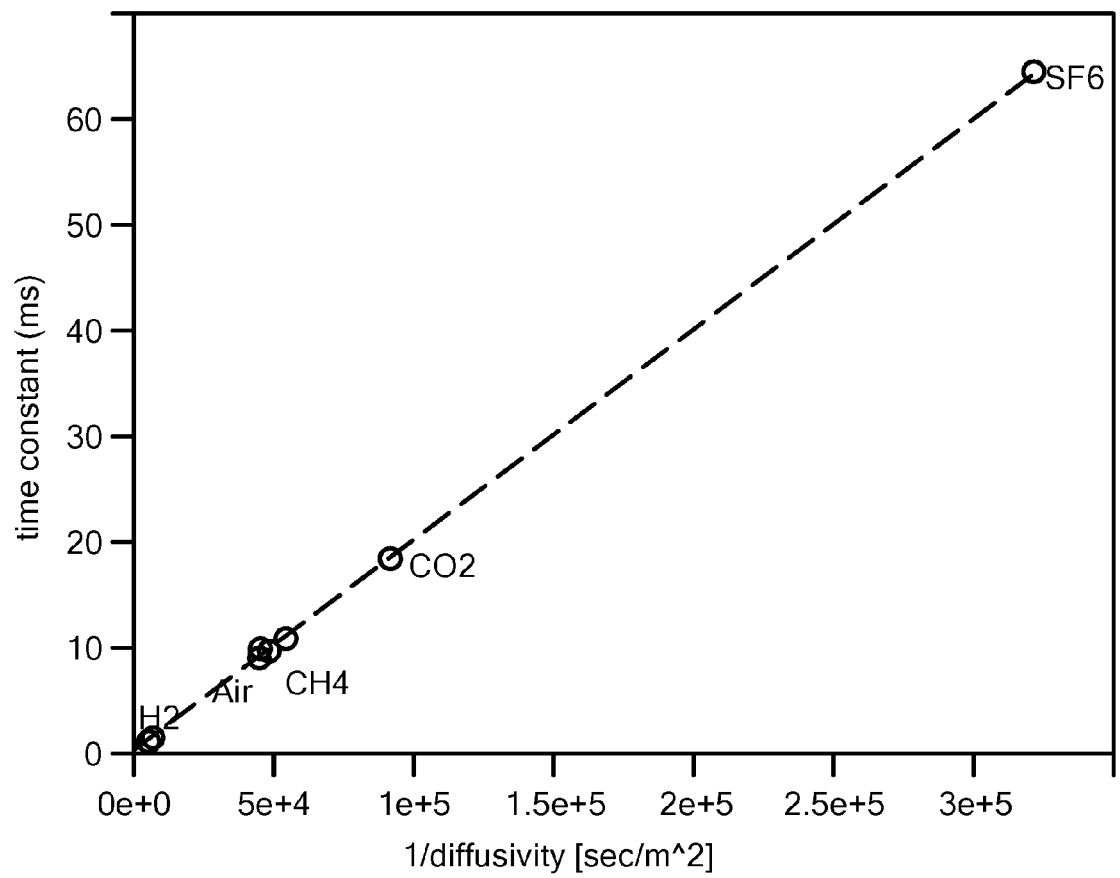
FIG. 6 Plot of simulated thermal time constant for a MEMS Flow Meter vs. 1/(gas thermal diffusivity) for several gases showing time constant is inversely proportional to gas thermal diffusivity.

FIG. 6 shows a plot of gas thermal time constant τ vs. 1/α, showing a direct proportion between these variables for seven different pure gases ($H_2$, He, Ar, $CO_2$, $CH_4$, $SF_6$, $N_2$)

of widely differing thermal diffusivities, plus one gas mixture (air) whose thermal diffusivity is known. These time constants came from a theoretical model of the coupled solid and fluid portions of the Memsic, Inc. thermal flow sensor, that takes account of their mutual thermal interaction.

Thus for any two gases 1,2 we may write $$\frac{\tau_1}{\tau_2} = \frac{\alpha_2}{\alpha_1} \quad (2)$$

To determine the relative thermal diffusivity of a gas being measured, it is necessary to first flow the gas in question into the flow sensing chamber and turn off the inlet and outlet positive shut-off valves. These will prevent any flow through the sensing volume while the gas thermal time constant is measured. A step change in heating power is then applied to the heater, and the temperature readings of the up and downstream temperature sensors are recorded as a function of time. This information is then processed by the Electronics and Computing Module (9 in FIG. 1) to yield the exponential thermal time constant for the gas in the chamber. The positive shut off valves may then be opened and the gas whose flow rate is required to be measured caused to flow through the sensor flow chamber, and the downstream—upstream temperature difference measured to provide the raw flow signal.

It was shown in FIG. 5 that there is a relationship between MEMS sensor output temperature difference ΔT and the flow variable Q/α of the form $$\Delta T = R(Q/\alpha) \quad (3)$$

Where R is a universal or gas-independent sensor response function for the MEMS thermal sensor in question. Therefore a measured value ΔT in general corresponds to different flows of different gases, such that for all gases with the same ΔT the ratio Q/α is constant. If, then, the universal function R has been determined by flow calibration with one gas (labeled by 1), We can find the flow of that gas corresponding to any particular ΔT by inverting the function R, ie. $Q_1 = \alpha_1 R^{-1}(\Delta T)$. Here $R^{-1}$ is the inverse function to R. The corresponding flow of gas 2 is then found from the relationship $$\frac{Q_2}{\alpha_2} = \frac{Q_1}{\alpha_1} \quad (4)$$

The ratio of α's is determined from the ratio of τ's, using (2)

$$Q_2 = \frac{\alpha_2}{\alpha_1} \cdot Q = \frac{\tau_1}{\tau_2} \cdot Q_1 \quad (5)$$

Thus if gas 1 is the calibration gas (whose thermal time constant has also been measured), it is possible to measure flows of any other gas once the time constant at 0 flow of said other gas is measured. In fact one can skip the thermal diffusivity altogether and write the universal response function in the alternate form $$\Delta T = R(Q\tau) \quad (6)$$

From Eq. (6) it is evident that given any unknown gas A whose thermal time constant at zero flow $\tau_A$ is measured in situ by the thermal flow sensor, one can invert the known universal function R to solve for $Q_A$ in terms of the measured flow sensor output ΔT as shown in Eq. (7)

$$Q_A = \frac{1}{\tau_A} \cdot R^{-1}(\Delta T) \quad (7)$$

By this method every distinct flow sensor output value ΔT is associated with a unique volume flow rate $Q_A$ of gas A, even though the flow sensor has never been directly calibrated with gas A. Similarly, if a thermal flow meter that has been calibrated on gas 1 is then used with gas 2, the volume flow rate of gas 2 that is flowing, $Q_2$, is then readily computed from the flow meter reading Q1, according to the simple expression $$Q_2 = \frac{\tau_1}{\tau_2} Q_1 \quad (8)$$

That is, the gas conversion factor for converting the reading Q1 of a MEMs thermal flow meter calibrated to measure gas 1, when the actual gas flowing through it is gas 2, is the ratio $\tau_1/\tau_2$, or equivalently the ratio $\alpha_2/\alpha_1$, from Equation (2).

Thus the gas conversion ratio needed to convert the volume flow rate measured with the meter calibration gas to the volume flow rate measured with any other gas measured with the same instrument, can either be determined in situ by directly measuring the thermal time constant of the process gas relative to the calibration gas, or from a reference table of gas thermal diffusivities, when the identity of the process gas is known and its thermal diffusivity relative to the calibration gas is tabulated. It is presumed that the identity of the calibration gas is known, that its thermal diffusivity is tabulated, and that its thermal time constant in the flow sensor has been measured and stored in the flow meter memory at the time of flow calibration. Similarly, it is presumed that the inverse function $R^{-1}(\Delta T)$ of the universal response function R(Q·τ) has been computed for the calibration gas, and stored in the flow meter on-board memory.

This invention teaches a novel method by which a MEMS thermal flow sensor that has been calibrated once accurately on a known fluid over a wide flow range may be used to measure flow of any other fluid or mixture even when the composition of that other fluid is not known, provided its thermal time constant may be measured in the flow sensor.

This is a substantial advance in the prior state of the art, that required a separate and expensive calibration on each gas before a MEMs flow sensor may be used to measure flow with different gases or mixtures of fluids, even when the composition of the gases was known, and their physical properties were tabulated.

Certain obvious extensions to the basic technique taught here for MEMS thermal flow sensors will occur to those skilled in the flow sensor art. These are claimed here as well as the simplest embodiment already described. For example, it is clear that this technique, in addition to being capable of measuring unknown fluids and mixtures, could also be applied to fluids and mixtures of known thermal diffusivity, by calculating in advance the ratios of their thermal diffusivities to that of the known calibration fluid, and storing them in instrument memory along with the universal dimensionless curve. Thus an instrument could be sold with such stored information on any set of different gases of interest to the user already stored in instrument memory, so as to permit immediate use on those known gases without requiring the extra time needed for an in situ time constant determination.

It will be evident as well to those skilled in the flow meter art that one could also use the capability of in situ fluid time constant determination and relation to the universal dimensionless curve as a means of self-checking on known fluids whose thermal properties are stored in instrument memory. For example, such a check of a new time constant determination against a prior time constant determination or stored thermal diffusivity value could reveal subtle shifts in the flow sensor characteristics due to sensor wear and tear with use that may indicate the need for a recalibration of the flow sensor.

Though the basic dimensionless relationship between flow sensor output and dimensionless flow through the sensor involves only the single fluid property thermal diffusivity, it is conceivable that more precise measurements will in future disclose a weaker dependence also on some additional fluid property or properties that may cause a subtle splitting of the universal sensor response curve for some sensor designs into multiple closely spaced curves. (This effect is familiar in atomic spectroscopy for example, where the basic optical line frequencies for Hydrogen are given to a first approximation by the Balmer formula, but subtle special relativistic effects cause some of the coincident Balmer lines to be split on a much finer wavelength scale into closely spaced multiplets. Hence to gain highest flow measurement accuracy it may become desirable in future to measure also one or more other fluid properties (such as fluid viscosity) in situ with the flow sensor, in addition to the relative thermal time constant or relative thermal diffusivity. For example one may include a differential pressure sensor to perform an in-situ measurement of the pressure drop occurring in the flow sensor, in order to estimate fluid viscosity, and so provide a more precise measure of the flow rate than could be achieved using the thermal diffusivity dependence alone to rescale the flow axis. Therefore any such additional in-situ fluid property measurements that may become desirable should properly be considered as lying within the scope of this invention, being merely an extension of the fundamental technique disclosed to additional fluid properties beyond thermal diffusivity.

Figure 7:
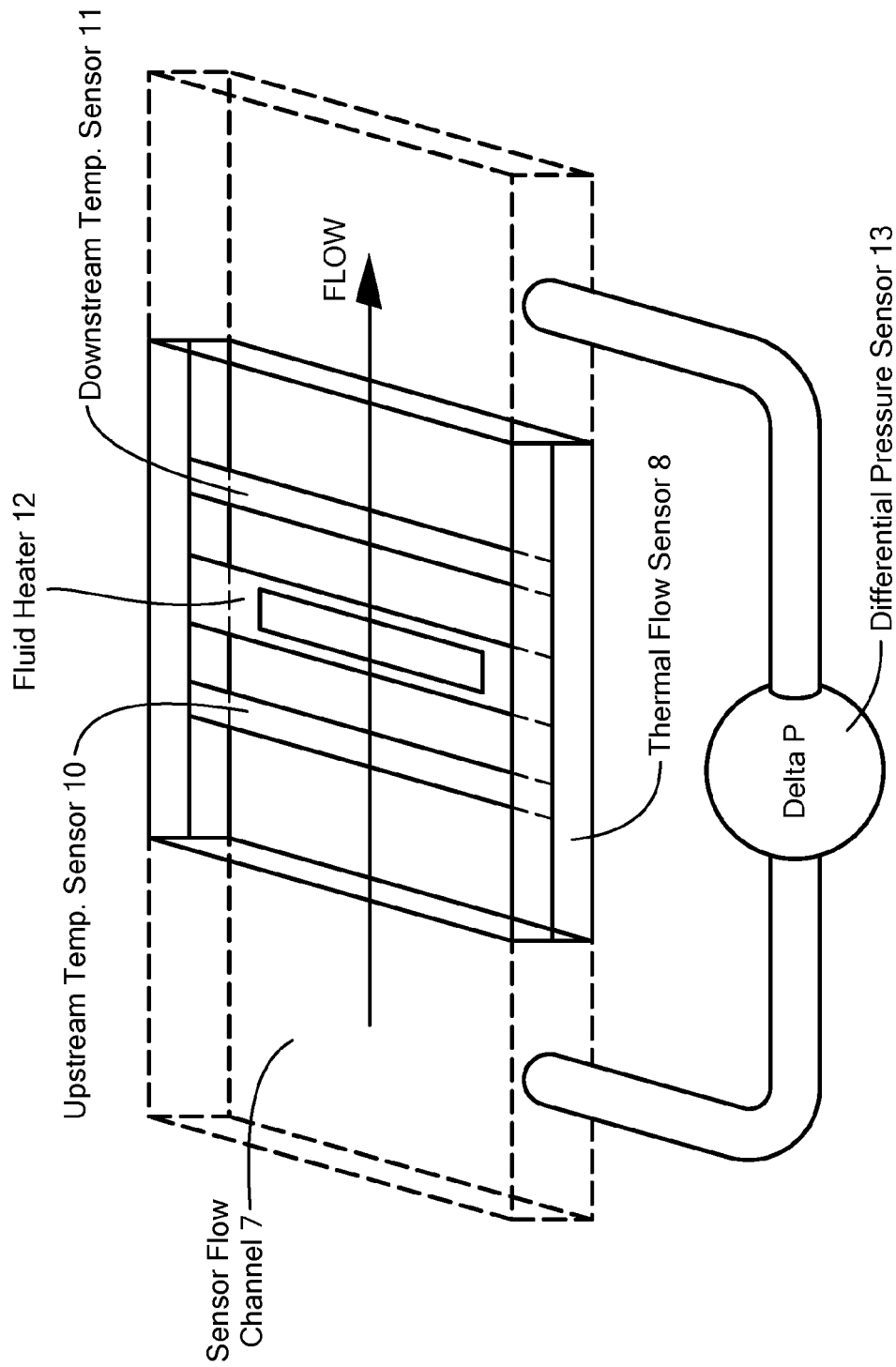
FIG. 7 shows the use of a supplementary differential pressure sensor 13 installed in parallel to the sensor flow channel to provide a measure of relative fluid viscosity in conjunction with the in-situ measurement of relative thermal diffusivity and volume flow rate, to provide higher flow accuracy in cases where gas viscosity causes minor splitting in the universal response curve.

FIG. 7 indicates a sensor where both relative fluid thermal diffusivity and relative fluid viscosity are measured in situ by the addition of a differential pressure sensor to measure the pressure drop occurring at a specific flow rate over the length of the sensor flow channel.

Figure 8:
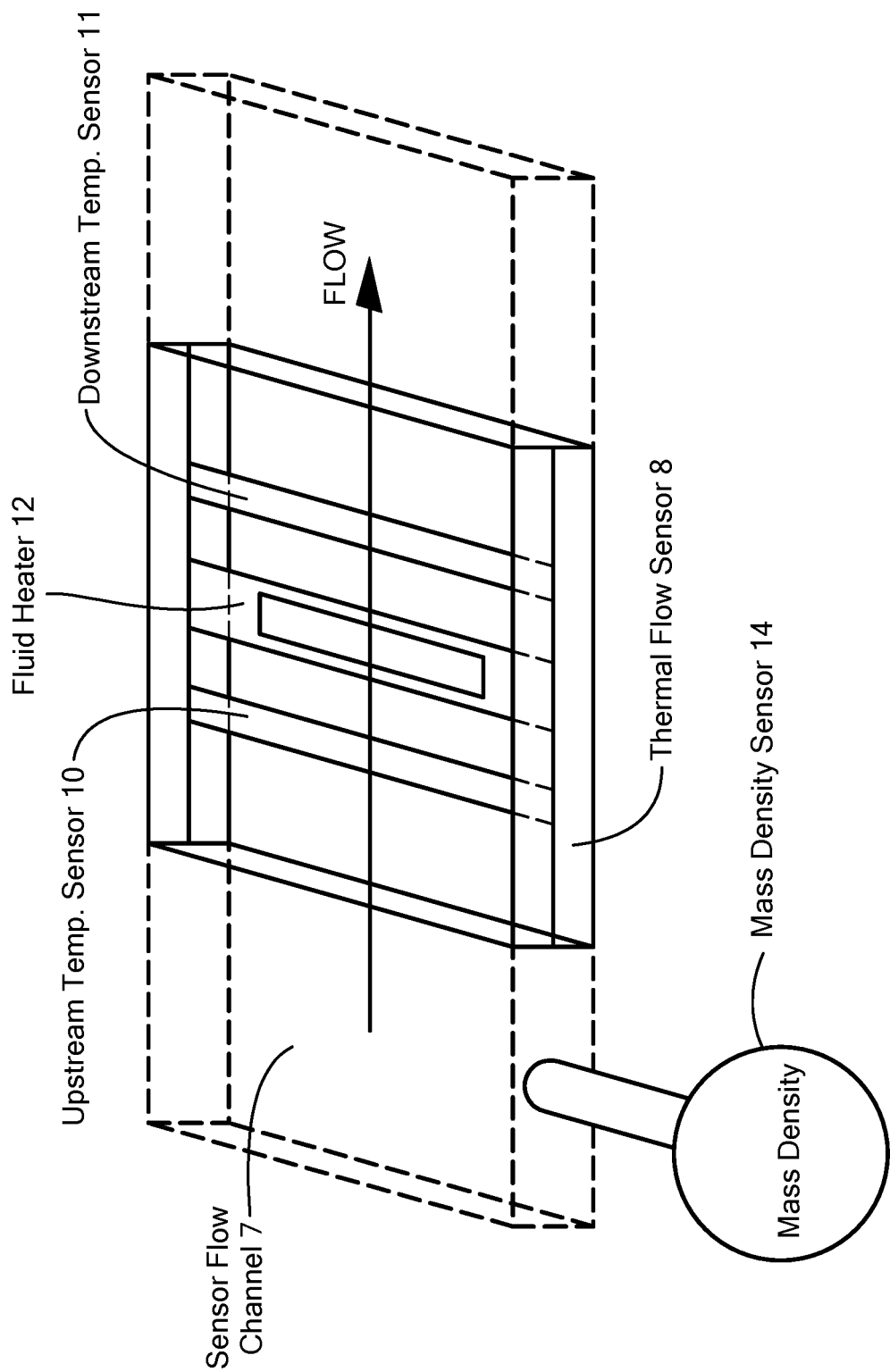
FIG. 8 Shows use of a supplemental fluid mass density measuring instrument 14 in combination with the volume flow rate measurement of the invention by means of in-situ measurement of fluid relative thermal diffusivity or thermal time constant, with the universal dimensionless response curve, to achieve measurement of mass flow rate of an unknown fluid.

FIG. 8 shows the use of an additional mass density sensor to measure the mass density of the flowing fluid in-situ. It will be evident as well to those skilled in the art, that having accurately measured volume flow rate of a known or unknown gas or gas mixture by use of the universal MEMS flow rate response curve $R(Q/\alpha)$ combined with an in-situ measurement of the relative thermal time constant of the known or unknown gas, one need only measure in addition the mass density of the fluid in situ to enable the gas mass flow rate to be determined, (computed as the product of mass density times volume flow rate). Therefore the combination of an in-situ mass-density measuring device with an in situ gas relative thermal time constant or relative thermal diffusivity measurement and a MEMS volume flow rate measurement using the universal response curve disclosed herein to achieve a mass flow measurement is also taught by this invention.

Figure 9:
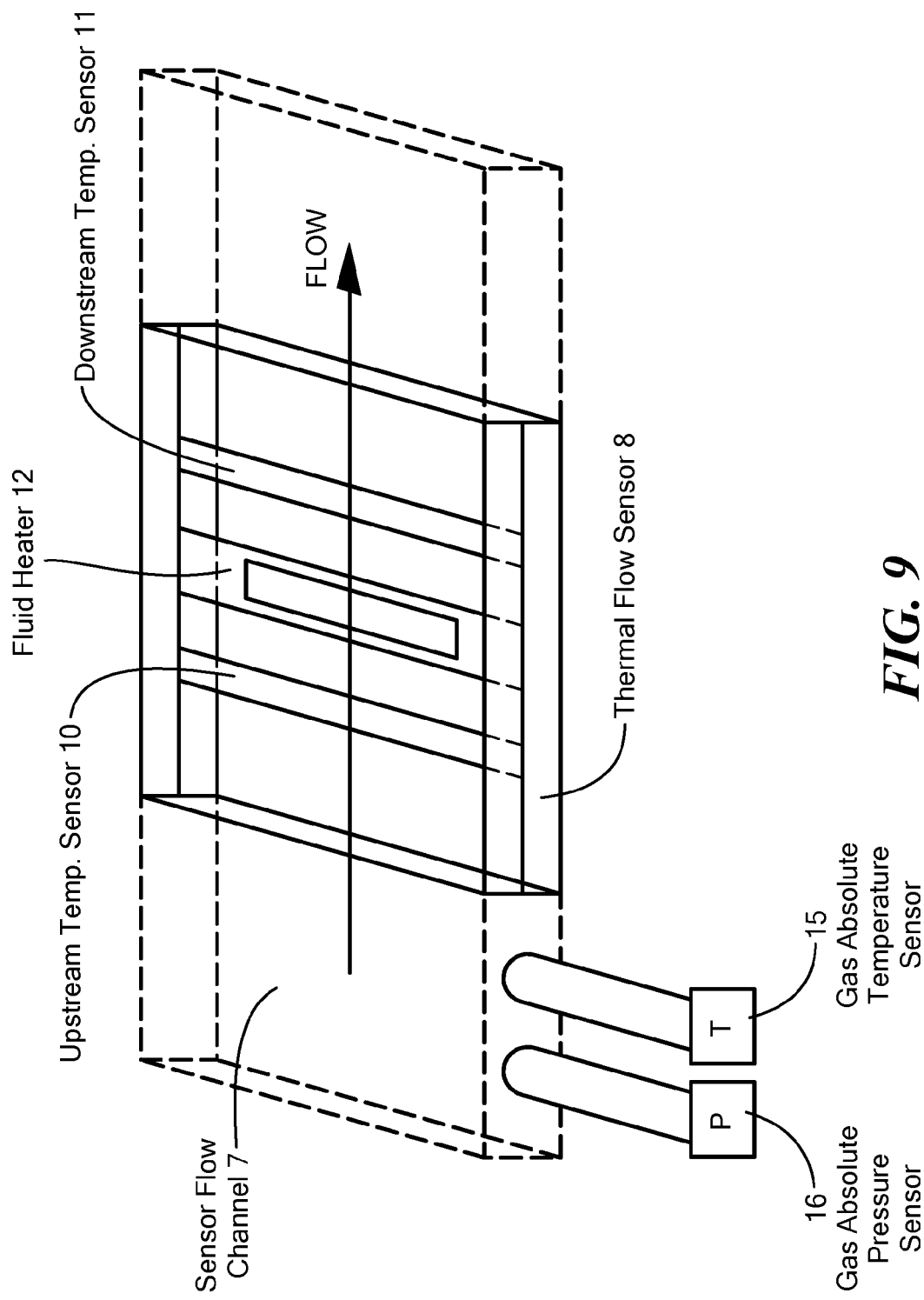
FIG. 9 For cases where the fluid is a perfect gas, it is possible to employ the known equation of state (9) with in-situ measurements of the gas temperature (T) and Pressure (P) and the volume flow rate Q to produce a flow signal directly proportional to the gas mass flow rate, and compensated for T, P variations.

FIG. 9 In cases where the chemical identity of a flowing gas is known, and also under conditions where the equation of state of the flowing gas may be adequately approximated by the perfect gas law (9)

$$P \cdot V = n \cdot Z \cdot R \cdot T \tag{9}$$

(where P=gas absolute pressure, T=gas absolute temperature, V=gas volume, n=# of mols of gas, Z=gas compressibility, (regarded as constant over a small range of P, T) R=universal gas constant), the in-situ measurement of fluid mass density may be replaced by 1) knowledge of the gas mass density at one specified reference temperature $T_0$ and pressure $P_0$; 2) in-situ measurements of the flowing gas Temperature and Pressure when the volume flow rate is determined; 3) Measurement of the known gas volume flow rate by use of the universal curve and relative thermal time constant of the flowing gas at pressure P and absolute Temperature T. In this case the perfect gas law (9) is used to determine from the measured volume flow rate Q of the gas at conditions (P,T) the equivalent volume flow rate of the gas $Q_0$ at reference conditions $P_0$, $T_0$. The mass flow rate is then the product of the known mass density $\rho_0$ at the reference conditions and the volume flow rate at those conditions, $Q_0$. To be specific, the equation used to compute $Q_0$ from Q measured at conditions P, T is (10)

$$Q_0 = \frac{P}{P_0} \cdot \frac{T_0}{T} \cdot Q \tag{10}$$

And the corresponding mass flow rate is $\rho_0 Q_0$.

Note that $Q_0$ of Equation (10) is directly proportional to the mass flow rate of a perfect gas (or mixture of perfect gases) even if the proportionality constant $\rho_0$ is not known. For flows of an unknown but perfect gas, therefore, in-situ measurement of P, T, and the gas thermal time constant $\tau$, combined with the knowledge of the universal MEMS flow sensor response curve measured by calibration with a known reference gas, provides the information to compute $Q_0$ for the unknown gas, the volume flow rate at the reference temperature and pressure. This signal is directly proportional to the mass flow rate of the unknown gas, compensated for gas temperature and pressure changes. Only the mass density of the unknown gas at the reference conditions remains unknown, and prevents a calibrated measurement of the mass flow rate of the unknown gas. However, for some purposes, (mass flow control compensated for temperature and pressure variations) an output signal directly proportional to mass flow rate may be sufficient. For example, one may manually adjust the mass flow rate of a key ingredient to balance a chemical reaction, then command a flow controller incorporating a MEMS flow sensor as a critical component to maintain the same mass flow set point (to keep the reaction balanced) despite changes in ambient P and T conditions. In this application it is not necessary to know the exact mass flow rate in kg/sec., only to correct any departures or drifts from the optimal mass flow rate setting. The case where supplemental gas inlet P and T measurements are combined with the volume flow rate Q and gas thermal time constant $\tau$ measurements at P, T with the MEMS thermal flow sensor output and the use of the universal response function to calculate $Q_0$ and $\rho_0 Q_0$ is illustrated in FIG. 9.

In the case where the fluid is known to be a perfect gas but otherwise unknown, and where the mass density is not known at any fiducial $P_0$, $T_0$, the configuration of FIG. 9 can still be applied to generate a flow output signal that is directly proportional to the mass flow at any fiducial point $P_0$, $T_0$, by calculating $Q_0$. This is a mass flow signal compensated for variations in fluid temperature and pressure, but not calibrated in kg/sec because the gas density is unknown. It can still be applied to make a mass flow controller that is not calibrated. Such a flow controller is still useful in situations where it is desired to hold the gas mass flow steady at an optimum value that can be determined by other means, for example by completeness of a gas phase chemical reaction. Therefore this method of producing a mass flow sensor that is not calibrated but is temperature and pressure compensated is still useful and within the scope of this invention.

The invention is not to be limited to what has been particularly described and is to embrace the spirit and full scope of the appended claims.

We claim:

1. A flow meter for measuring flow rate of a fluid comprising:
   a body having a flow channel through which a fluid can flow and having a flow sensing chamber;
   first and second valves at respective inlet and outlet ends of the flow sensing chamber, the valves being operative in an open position to permit fluid flow through the chamber, and operative in a closed position to block fluid flow through the chamber;
   a MEMS thermal flow sensor disposed in the flow sensing chamber in contact with fluid therein and providing a sensor signal representative of fluid flow rate;
   a processor including a memory and operative to store data representative of a sensor response curve, and to store data representing the thermal time constant of a calibration fluid;
   the processor operative to control the opening and closing of the first and second valves and to measure the thermal time constant of a measured fluid in the flow sensing chamber when the first and second valves are closed and to store that measured thermal time constant data, and operative to provide a conversion factor derived from the ratio of the thermal time constant of the calibration fluid to the measured thermal time constant, and operative to adjust the reading of the sensor signal in accordance with the conversion factor and sensor response curve to produce an output signal which represents the correct flow rate of the measured fluid.

2. The flow meter of claim 1 wherein the MEMS thermal sensor comprises:
   a fluid heater;
   a first temperature sensor disposed upstream of the heater;
   a second temperature sensor deposed downstream of the heater.

3. The flow meter of claim 2 wherein the first and second temperature sensors are equally spaced respectively upstream and downstream of the fluid heater.

4. The flow meter of claim 1 including a fluid mass density measuring instrument providing mass density data to the processor to enable the processor to produce an output signal which represents mass flow rate of the measured fluid.

5. The flow meter of claim 1 wherein the measured fluid can be considered a perfect gas, and including:
   a pressure sensor for providing to the processor data representing the pressure of the measured fluid in the flow channel;
   a temperature sensor for providing to the processor data representing the temperature of the measured fluid in the flow channel;
   whereby the processor can produce an output signal which represents mass flow rate of the measured fluid.

6. The flow meter of claim 2 wherein the processor is operative to measure thermal time constant of a measured fluid by measuring power to the fluid heater after the first and second valves are closed.

7. The flow meter of claim 1 wherein the flow channel in the body is a bypass channel in parallel with a bulk flow channel in the body.

8. The flow meter of claim 1 including a differential pressure sensor for measuring the upstream and downstream pressure of fluid flowing in the flow channel and providing to the processor data representing relative fluid viscosity.

9. A method for measuring the flow rate of a fluid flowing through a channel in which a MEMS thermal flow sensor is disposed in contact with the fluid, the method comprising the steps of:
   introducing a fluid in the flow channel;
   trapping a quantity of fluid in the channel to provide a zero flow condition;
   measuring the thermal time constant of the fluid in its zero flow condition;
   providing a ratio of the measured thermal time constant of the fluid to a thermal time constant of a calibration fluid stored in memory to produce a conversion factor;
   providing a sensor response curve for a fluid having a known thermal time constant;
   adjusting a reading of a sensor signal of the MEMS thermal flow sensor in accordance with the conversion factor and sensor response curve to produce an output signal which represents the correct flow rate of the measured fluid.

* * * * *